United States Patent [19]

Coe

[11] 4,155,245
[45] May 22, 1979

[54] DEWPOINTMETERS

[75] Inventor: Charles D. Coe, Sheffield, England

[73] Assignee: Land Pyrometers Limited, Sheffield, England

[21] Appl. No.: 850,628

[22] Filed: Nov. 11, 1977

Related U.S. Application Data

[63] Continuation-in-part of Ser. No. 695,303, Jun. 11, 1976, abandoned.

[30] Foreign Application Priority Data

Jun. 18, 1975 [GB] United Kingdom ............... 26013/75

[51] Int. Cl.² .......................................... G01N 25/68
[52] U.S. Cl. .................................................. 73/17 A
[58] Field of Search ....................................... 73/17 A

[56] References Cited

U.S. PATENT DOCUMENTS

| 2,240,082 | 4/1941 | Thornwaite | 73/17 |
| 2,435,895 | 2/1948 | McIlvaine | 73/17 |
| 2,750,546 | 6/1956 | Washburn | 73/17 |
| 2,979,950 | 4/1961 | Leone | 73/17 |
| 3,083,565 | 4/1963 | Jennings et al. | 73/17 |
| 3,319,457 | 5/1967 | Leone | 73/17 |
| 3,930,398 | 1/1976 | Levina et al. | 73/17 |

*Primary Examiner*—Herbert Goldstein
*Attorney, Agent, or Firm*—Lowe, King, Price & Becker

[57] ABSTRACT

A dewpointmeter comprises a detecting element or probe, a thermocouple adapted to determine the temperature of the probe, means for directing a flow of cooling air at the probe, and an electrical circuit extending to the probe and adapted to be completed by condensate formed on the probe, there being a motor driven regulator adapted to control the rate of flow of cooling air directed at the probe, which motor is adapted to be driven in accordance with the current flowing through the circuit.

19 Claims, 10 Drawing Figures

DEWPOINTMETERS

This application is a continuation-in-part of application Ser. No. 693,303 filed June 11, 1976, now abandoned.

This invention relates to dewpointmeters.

It is important in various instances to provide a means of determining the dewpoint of a gas, which has been defined as the highest surface temperature at which it is possible to condense a liquid film on a surface exposed to the gas. Thus, knowledge of the dewpoint of a flue gas is important in such areas as the study of low temperature corrosion in boilers, it being the case that if the flue gas is at a temperature lower than the dewpoint, the gas will condense and the acidic nature of the condensate can cause corrosion of the metal parts of a flue. Also, when the inner surface of the flue is wet, the fine solid particle content of the gas is caused to adhere on the inner surface—a feature which should be avoided.

Hitherto, it has been usual to utilise a dewpointmeter to determine the dewpoint of, e.g. a flue gas, and predominantly such dewpointmeters have been manually operated, although attempts have been made to provide an automatic dewpointmeter. Standard manual dewpointmeters, such as shown in British Standard BS1756, Part IV, 1965 consist of two base elements, a detecting element including an electrical circuit to be completed by condensate formed on it, to be inserted in the gas stream, and against which cooling air is directed, and a box containing measuring instruments and the controls. With the detecting element inserted in the gas stream, and allowed to warm up cooling air is then directed against the detecting element to cool the element until a conducting film has condensed on it. The air flow is then manually regulated until a steady current reading is obtained at which point the rate of condensation and the rate of evaporation of the condensate is equal, and when the temperature of the detecting element is at the dewpoint temperature of the flue gas. The steady current reading can then be utilised to determine the dewpoint of the gas. Whilst such devices function adequately, it is a major disadvantage that the operation is non-continuous. An operative is required to switch off the air flow to allow the element to heat up, reapply the air flow and adjust the air flow to obtain the steady reading each time a reading is required to be taken.

In an attempt to provide an automatic dewpointmeter, it has been proposed to provide a detection circuit to sense the onset of condensation on the element, the circuit causing the temperature of the element to be taken simultaneously with the onset of current, and at the same time activate a solenoid valve to switch off the flow of cooling air to the element. The temperature of the element thus begins to increase until it is raised above the dewpoint temperature and all the condensate evaporates. The cooling air is then automatically switched on again to cool the element until again there is the onset of condensation and thus current, and the cycle repeated. Thus, a semi-continuous measurement of dewpoint temperature is obtained in that at each point in the cycle that the element is at the dewpoint temperature, condensate appears and the temperature read. The disadvantage of this method is that, apart from being semi-continuous, the time lag involved in detecting the onset of condensation causes the temperature to be read at a point below the dewpoint temperature, and this error, which can be of the order of 5° C. to 10° C. is dependent on the rate of build up of condensate and the rate of cooling of the element.

It has also been proposed (British Pat. No. 1,405,492) in an attempt to provide an automatic system, to provide a circuit that measures the current in a circuit completed by condensate on the element, the circuit controlling the switching on and off of the cooling air. Thus, when current in the circuit reaches a pre-set maximum, a solenoid valve is activated to switch off the cooling air to the element. As the temperature of the element rises condensate begins to evaporate and proportionately less current flows in the circuit until it reaches a pre-set minimum, when the solenoid valve is operated to switch on the cooling air. In this way the current oscillates between the pre-set value, and the temperature of the element oscillates above and below the dewpoint temperature. This temperature oscillation can be as high as +15° C. about the dewpoint temperature, and makes accurate determination of the dewpoint temperature almost impossible.

According to the present invention, a dewpointmeter comprises a detecting probe, a thermocouple adapted to determine the temperature of the probe, means for directing a flow of cooling air at the probe, and an electrical circuit for supplying a current to the probe, said circuit adapted to be completed by condensate formed on the probe: a regulator driven by a motor for controlling the rate of flow of cooling air directed at the probe, and means for controlling the motor driven regulator in accordance with the current flowing through the circuit, said controlling means including electronic means for measuring a rate of change of the measured current, said controlling means being responsive to the magnitude and sign of the measured rate of change for controlling respectively the speed and direction of the regulator motor.

Thus, when the differential with respect to time of the current is positive, the element must be below the dewpoint temperature, and the motor is driven to decrease the flow of cooling air to the element. Thus the element heats up to a point where the condensate begins to evaporate, and when the differential of the measured current becomes negative, showing that the element is above the dewpoint temperature. That signal causes the direction of the motor to be reversed, to increase the flow of cooling air to the element, and thus cool it down. By utilising a motor driven regulator, controlled as defined above, the cooling air can be blown at the element at a rate to maintain the temperature of the element substantially constant, that temperature being the one at which the current in the circuit is substantially constant, and at which the rate condensate is forming is equal to the rate at which it is evaporating, i.e. the dewpoint temperature.

It is however possible to utilise an additional so-called proportional control for the motor. Thus, means can be provided in the circuit to detect when the current in the circuit is above or below a pre-set threshold current of a value at a level high enough not to be affected by the slow increase of stray current due to contamination of the element surface with solid particles when inserted in the flue gas.

By providing both forms of control over the motor driven regulator, the differential control preventing any tendency for the temperature of the element to oscillate above and below the dewpoint temperature as may be possible in certain circumstances when proportional control only is provided, and the proportional control ensuring that if in certain circumstances the condensate is reduced to zero by the element temperature being above the dewpoint temperature, and thus the current and the rate of change of current being zero, the differential control will become inoperative, leaving the proportional control to reduce the temperature of the element to the dewpoint temperature whereupon condensate is again formed and the differential control becomes operative once more.

The motor of the motor driven pressure regulator may be a variable speed motor operated by a continuous drive signal, or a synchronous motor operated by feeding in a train of pulses, and when the speed of the motor is proportional to the "ON/OFF" ratio of the train of pulses.

The reading from the thermocouple may be visually displayed, or arranged to provide a permanent record on a chart recorder. Obviously, both a visual and permanent record can be provided if desired.

To ensure that the probe does not become fouled by dirt, it is preferred to provide for the cleaning of the probe at regular intervals. Thus, an adjustable timer may be provided, and the probe fitted with a cleaning air or other fluid tube directed at the detector element of the probe, so that at regular intervals, cleaning air or other suitable fluid, e.g. water is blown against the element. Typically a cleaning blow will last for 10 seconds with a frequency of one blow every 3 hours.

If desired, the probe may additionally be provided with an external thermocouple to obtain approximate reading of gas temperature in the vicinity of the probe.

One embodiment of the invention will now be described with reference to the accompanying drawings in which.

Figure 1:
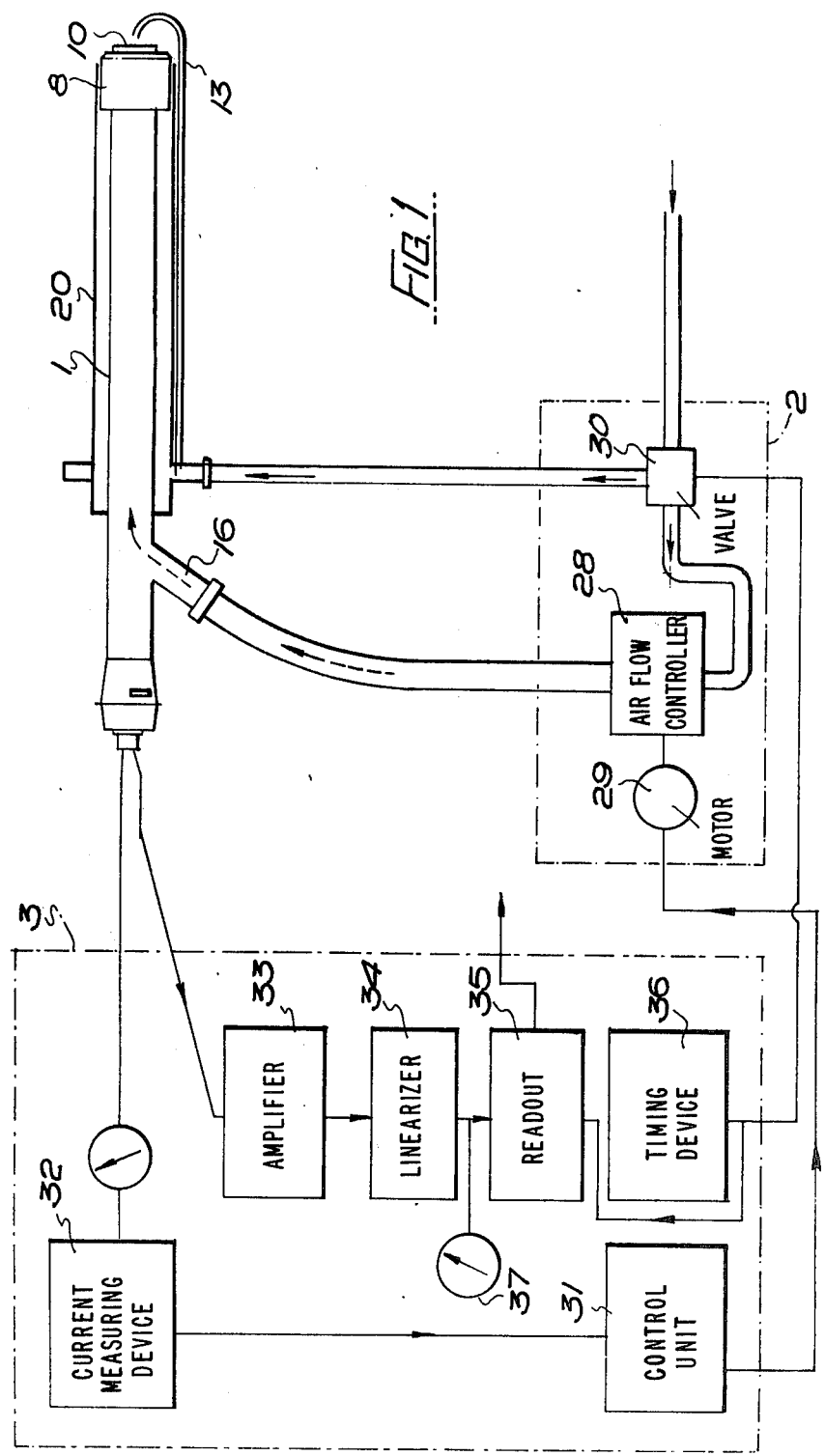
FIG. 1 is a general arrangement showing schematically a dewpoint in accordance with the invention.

In the drawings, a dewpointmeter includes a probe tube 1 for insertion in a stream of, e.g. flue gas, the probe tube being connected to a source of cooling air governed by a motor-driven regulator unit 2, and there being an electronic control unit 3, described in greater detail below.

Figure 2:
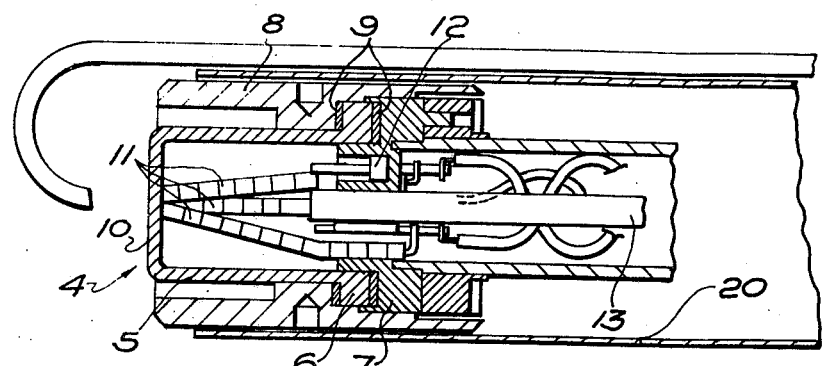
FIG. 2 is a sectional side elevation of the detecting element in the end of the probe tubes of FIG. 1.
Figure 3:
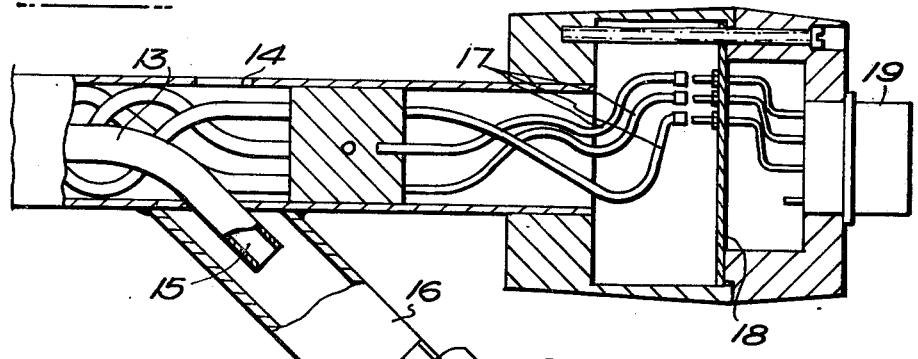
FIG. 3 is a sectional side elevation of the probe connecting means.
Figure 9:
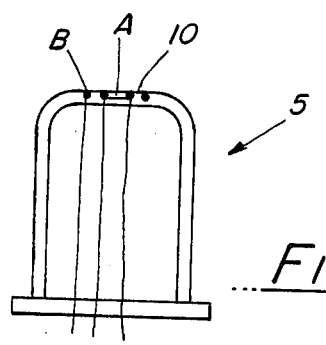
FIG. 9 is a cross-sectional side view of the sensor showing the annular electrode and thermocouple.
Figure 10:
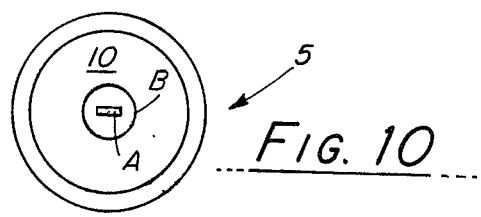
FIG. 10 is a top view of the sensor shown in FIG. 9.

As is shown particularly by FIGS. 2 and 3, the probe tube 1 is provided with a detecting element 4 formed by a thimble 5 of borosilicate glass, having a collar 6 lying between a shoulder on a stainless steel terminal block 7 mounted on the probe tube, and an internal shoulder on a locking collar 8, there being asbestos seals 9 between the collar 6, the terminal block 7 and the locking collar 8. Referring to FIGS. 9 and 10, the end of the thimble 5 is formed by a disc 10 of sintered glass into which is fused a platinum/rhodium thermocouple A, and an annular platinum electrode B, the platinum leg of the thermocouple, and the annular platinum electrode forming the two electrodes across which a stabilised A.C. potential is applied. Three platinum leads 11 extending from the detecting element are insulated by ceramic material and are silver soldered to terminals 12 mounted on the terminal block 7.

The probe tube 1, of stainless steel, is provided with an inner tube 13 carrying cooling air to the thimble 5, to direct cooling air at the inner face of the glass disc 10. Air admitted to the thimble exhausts through apertures in terminal block into the probe tube 1, and to atmosphere through holes 14 in the probe tube (see FIG. 3). Also as is shown more particularly by FIG. 3, the inner tube 13 has an inlet 15 extending out of the probe tube 1 to an air supply pipe 16 terminating in a quick release coupling 17 incorporating a self-sealing valve.

Extension leads 17 from the terminals 5 pass down the probe tube 1 to a terminal board 18, the board having appropriate leads to a socket 19, to enable connection of the probe to the electronic control unit 3. Preferably, a thermistor, not shown, is provided on the board 18 to constitute a cold junction compensator for the thermocouple.

Figure 4:
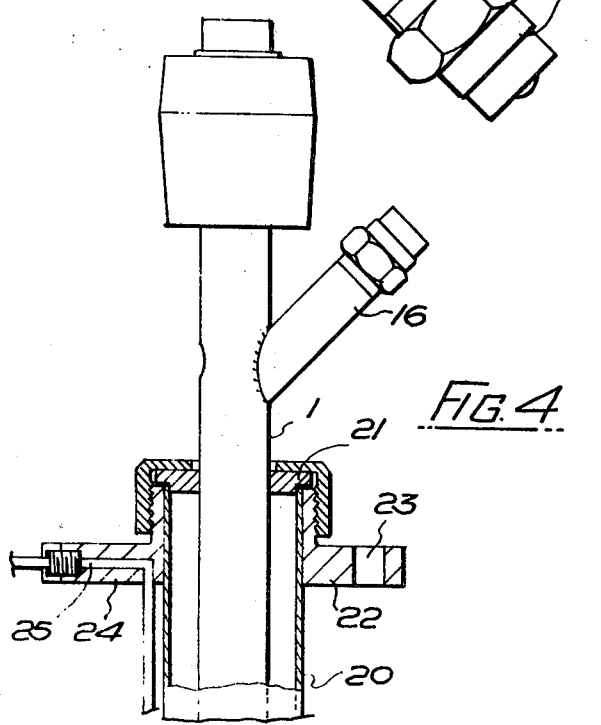
FIG. 4 is a sectional side elevation of the connection of the probe tube to a probe adaptor tube.

As is shown particularly by FIG. 4, the probe tube 1 is located in position by a probe adaptor tube 20. Thus, an end cap 21 is provided on the adaptor tube 20, having an aperture through which passes the probe tube 1, the end cap also locating a flanged member 22 provided with appropriate holes 23 by which the adaptor tube can be bolted in position. As is shown particularly by FIG. 2, the locking collar 8 is a close fit in the opposite end of the adaptor tube 20. The flange 24 of the member 22 has an air passageway 25 connected to a source of compressed air, and to which an air passageway or tube 26 is connected, the tube 26 having its opposite end 27 directed against the outer surface of the thimble 5.

As is shown schematically by FIG. 1, the air supply pipe 16 is connected to an air flow controller 28 within the motor driven regulator 2, the controller 28 being driven by a motor 29 (manufactured by Philips Electrical Industries, model number 9904–11104331). Within the unit 2 is a solenoid valve 30 controlling the passage of air to the tube 26. The electronic control unit 3 comprises a control unit 31 for the motor 29 activated by current measurement means 32 connected to the detecting element 4 on the probe tube. The thermocouple A on the glass disc 10 is connected to an amplifier 33 in the unit 3, which in turn is connected to a linearizer 34, the linearizer feeding a device 35 providing a temperature read-out facility. Also within the unit 3 is a timing device 36 coupled to the solenoid valve 30.

Thus, with the probe tube 1 secured by the adaptor tube 20, to, e.g. the wall of a furnace flue (not shown) such that the detecting element 4 is situated in the flow of flue gas, compressed air is fed to the air flow controller 28 and thus to the thimble 5. Cooling of the thimble causes condensate to form on the outer surface of the thimble to complete an electrical circuit from the electronic control unit by bridging the platinum leg of the thermocouple A and the platinum annulus B on the glass disc 10. Therefore, current fed to the circuit from the control unit 3 passes through the circuit at a rate determined by the amount of condensate on the thimble. The current measuring device 32 serves two additional functions. Firstly, it includes electronic means to determine the differential of the current measured, and secondly, it includes means to determine whether or not the current measured is above or below a pre-set threshold level. Whilst current is flowing in the circuit, the differential of the current may be positive, zero or negative. A positive differential indicates that the temperature of the thimble is below dewpoint, and a negative differential that the thimble is above dewpoint. In either instance, a signal is fed to the controller 31 which in turn controls the direction of drive of the motor 29 and the speed of drive in accordance with the sign of the differential and its magnitude. A zero differential, in normal circumstances indicates that the thimble is at the dewpoint temperature, and no signal is passed to controller 31 causing the drive of the motor and hence the setting of the regulator 28 to be maintained in the condition that has created the zero differential of the current. However, in abnormal circumstances, the thimble could be brought very rapidly to a temperature at which all the condensate has evaporated. Thus, a zero reading for current would be taken, and the electronic means within the device 32 produce a zero differential. This could lead to the drive of the motor 29 and the setting of the regulator 28 to be maintained in a condition whereby the thimble is maintained at a temperature where no condensate can form. However, by providing means in the device 32 to determine that the current is above or below a threshold level, a zero reading of current would cause a signal to be passed to the controller 31 to cause the drive of the motor 29 and hence the setting of the regulator 28 to increase the flow of cooling air to the thimble to cool it down and when condensate would again be formed. As soon as condensate is formed, the differential form of control would then become the predominant control factor once more.

By effectively controlling the motor 29 by the current in the circuit completed by the condensate on the thimble, there is continuous correction of the motor drive and hence continuous adjustment of the rate at which cooling air is directed into the thimble 5, the result of which is that the thimble is held at substantially a constant temperature, that at which the rate of condensation is equal to the rate of evaporation of the condensate, this being the dewpoint temperature of the particular flue gas being measured.

The thermocouple A on the glass disc 10 continuously reads the temperature of the gas, and feeds its signal to the amplifier 33, from where the signal is directed through the linearizer 34 and to the read-out device 35. If required a temperature gauge 37 can be provided in addition to the read-out (e.g. a pen recorder) from the device 35.

The invention, therefore, provides a relatively simple means of providing for the continuous detection measurement and display of the dewpoint temperature of any gas.

To provide for the cleaning of the outer face of the glass disc 10, the timing device is set such that at regular intervals, the solenoid valve is operated to allow a blast of cleaning air to be directed at the disc 10, the timer also controlling the duration of the blast.

Figure 5:
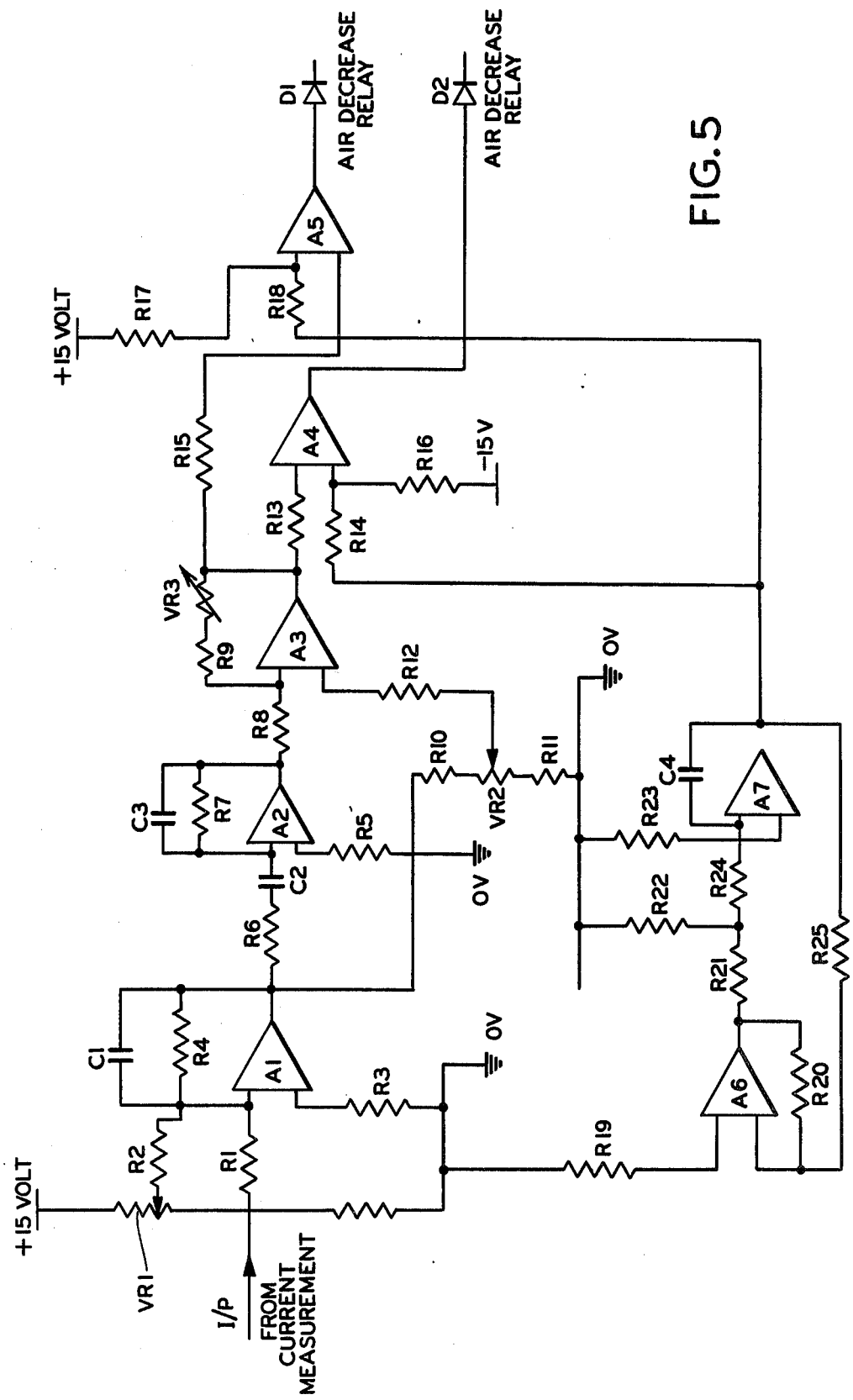
FIG. 5 is a circuit diagram showing the control circuit for the motor driven regulator of FIG. 1.
Figure 6:
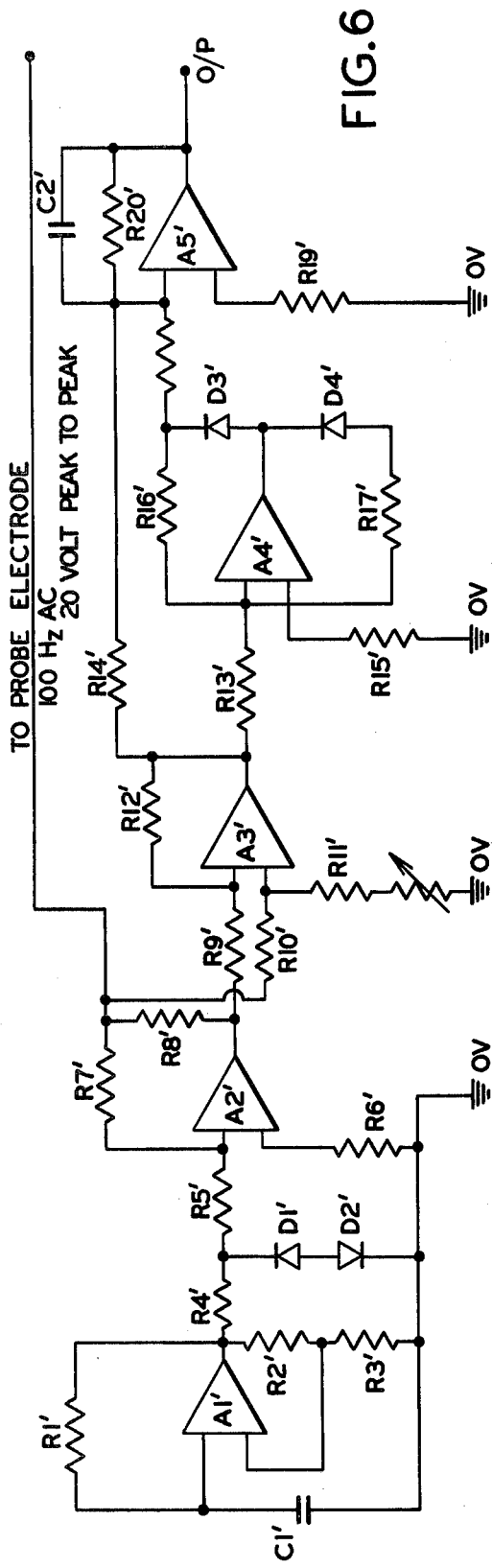
FIG. 6 is a circuit diagram showing the current measurement circuit.
Figure 7:
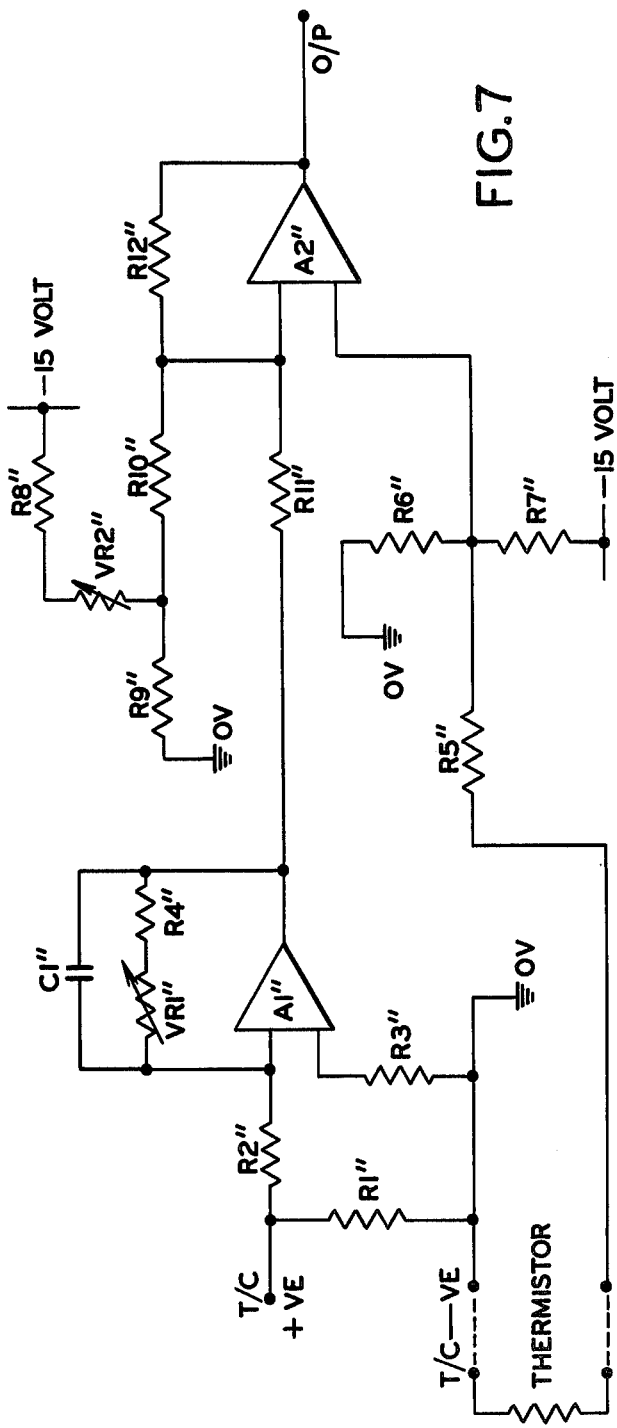
FIG. 7 is a circuit diagram of the thermocouple and amplifier of FIG. 1.

In FIGS. 5 to 7, are shown the circuits for the control of the motor driven regulator, current measurement and thermocouple/amplifier respectively.

Thus, in FIG. 5 the control set point for the proportional mode of control is governed by a comparator amplifier A1, which compares the current measured value against the set point and amplifies the difference between the signals. The value of the set point is adjusted by the patentiometer VR1, and is usually set at $100\mu$ amp. The sign of the output of amplifier A1 depends upon whether the current measured value is greater or less than the set point.

Capacitor C2, resistor R7 and amplifier A2 form a differentiator circuit, R6 and C3 supplying some signal smoothing. The output of A2 is the time differential of the current measurement. Amplifier A3 provides a summary point at which the proportional signal from A1 and the differential signal from A2 are added to form a composite control signal. The gain of the proportional circuit is adjusted by the potentiometer VR2 and the overall system gain by potentiometer VR3.

The air flow to the probe is controlled by a pressure regulator driven by a synchronous motor. The rate of change of air flow is adjusted by pulsing the motor at constant frequency of about 1Hz at varying on/off ratios. This is achieved by comparing the control signal against a triangular waveform.

Amplifiers A6 and A7 and resistors R19, R20, R21, R22, R23, R24, R25 and capacitor C4 form a triangular wave generator, where output is fed to two further amplifiers A4 and A5, to be compared with the control signal from A3. A4 and A5 form switching amplifiers which drive the relays to operate the synchronous motor to regulate the air flow of the probe.

Figure 8:
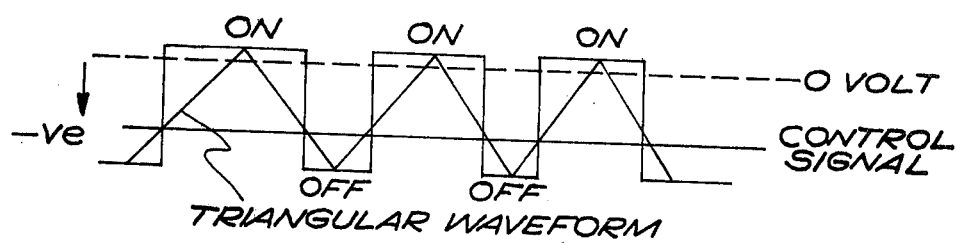
FIG. 8 is a schematic representation of the triangular waveform and its cooperation with the control signal.

At A4, for periods when the control signal is more negative than the signal from A7, the amplifier switches on the motor to increase the air flow, the triangular waveform thus causing the amplifier A4 to switch on and off at the frequency of the triangular wave but at a mark space ratio governed by the magnitude of the control signal as illustrated in FIG. 8.

Amplifier A5 acts in a similar manner but operates a relay to decrease the air flow when the control signal is more positive than the triangulor wave.

To provide for current measurement (FIG. 6) a 100 Hz A.C. potential is generated by an oscillator formed by amplifier A1' and components R1', R2', R3' and C1'. The potential is stabalised by zener diodes D1' and D2' and is fed to the probe electrodes after further amplification by amplifier A2'. The current flowing between the electrodes is measured from the voltage across resistance R8 which is in series with the probe electrodes. This voltage signal is amplified by the differential amplifier formed by R9', R10', R11' and R12' and amplifier A3'. VR1' provides zero adjustment to give zero volts at the output of A3' when the probe electrodes are open circuit. Rectification is provided by diodes D3' and D4' and amplifier A4' while R20' and C2' and amplifier A5' provide the necessary smoothing for the final current measurement value.

As is shown by FIG. 7, the thermocouple output is fed directly to amplifier A1'', the amplification being adjusted by the potentiometer VR1''. The output at this stage is then fed to a summing amplifier A2'' where the signal is compensated for variations in the cold junction temperature at the thermocouple. The cold junction temperature is measured at the probe by a thermistor. Zero adjustment is provided by potentiometer VR2'', which biases the amplifier A2''.

What we claim is:

1. In a dewpointmeter comprising a detecting probe, a thermocouple adapted to determine the temperature of the probe, means for directing a flow of cooling air at the probe, and an electrical circuit for supplying a current to the probe, said circuit adapted to be completed by condensate formed on the probe, an amount of current supplied to the probe by said circuit being a function of an amount of condensate formed on said probe; a regulator driven by a motor for controlling the rate of flow of cooling air directed at the probe, means for measuring a current flowing through the circuit and means for controlling the motor driven regulator in accordance with the measured current flowing through the circuit, said controlling means including electronic means for measuring a rate of change of the measured current, said controlling means being responsive to the magnitude and sign of the measured rate of change for controlling respectively the speed and direction of the regulator motor.

2. A dewpointmeter as in claim 1, wherein said controller means further includes detector means in the circuit to detect when the current in the circuit is above or below a pre-set threshold current having a value at a level high enough not to be affected by the slow increase of stray current due to contamination of the probe surface with solid particles when inserted in the flue gas, said regulator motor being controlled by said detector means.

3. A dewpointmeter as in claim 1, wherein the motor driven pressure regulator includes a variable speed motor operated by a continuous drive signal.

4. A dewpointmeter as in claim 1, wherein the motor driven pressure regulator includes a synchronous motor operated by feeding in a train of pulses, the speed of the motor being proportional to the "ON/OFF" ratio of the train of pulses.

5. A dewpointmeter as in claim 1, wherein a reading from the thermocouple is visually displayed.

6. A dewpointmeter as in claim 1, wherein a reading from the thermocouple is arranged to provide a permanent record on a chart recorder.

7. A dewpointmeter as in claim 1, wherein the probe is fitted with a cleaning fluid tube directed at a detector element of the probe.

8. A dewpointmeter as in claim 7, wherein an adjustable timer is provided to periodically admit cleaning fluid along the tube.

9. A dewpointmeter as in claim 7, wherein an adjustable timer is provided to determine the length of time that cleaning fluid is passed along the tube.

10. A dewpointmeter as in claim 1, wherein an external thermocouple is provided to obtain approximate readings of gas temperatures in the vicinity of the probe.

11. A dewpointmeter as in claim 1, wherein the probe is provided with a detecting element in the form of a thimble.

12. A dewpointmeter as in claim 11, wherein the thimble is formed from borosilicate glass.

13. A dewpointmeter as in claim 11, wherein the end of the thimble is formed by a disc into which is fused a thermocouple and an annular electrode.

14. A dewpointmeter as in claim 13, wherein the disc is of sintered glass.

15. A dewpointmeter as in claim 13, wherein the thermocouple is a platinum/rhodium thermocouple.

16. A dewpointmeter as in claim 13, wherein the annular electrode is of platinum.

17. A dewpointmeter as in claim 1, wherein the probe is formed as a tube and is provided with an inner tube for the passage of cooling air.

18. A dewpointmeter as in claim 1, wherein an adapter tube is provided to locate the probe in its position of use.

19. In a dewpointmeter comprising a detecting probe, a thermocouple adapted to determine the temperature of the probe, means for directing a flow of cooling air at the probe, and an electrical circuit for supplying a current to the probe, said circuit adapted to be completed by condensate formed on the probe, an amount of current supplied to the probe by said circuit being a function of an amount of condensate formed on said probe; a regulator driven by a motor for controlling the rate of flow of cooling air directed at the probe, means for measuring said probe current and means for controlling the motor driven regulator in accordance with the measured current, said measured current being composed of a first current component related to the condensate formed on the probe and a second current component related to contamination of the probe surface with particles when said probe is inserted in the flue gas, said controlling means including first means responsive to the measured current for controlling the motor and second means for monitoring said measured current for enabling said first means to control said motor, said second means including means for generating a reference current having a magnitude related to the magnitude of said second current component and means for comparing said reference current to said measured current.

* * * * *